United States Patent [19]

Perlin

[11] 4,304,239

[45] Dec. 8, 1981

[54] ESOPHAGEAL PROBE WITH BALLOON ELECTRODE

[75] Inventor: Alfred R. Perlin, Highland Park, Ill.

[73] Assignee: The Kendall Company, Boston, Mass.

[21] Appl. No.: 128,007

[22] Filed: Mar. 7, 1980

[51] Int. Cl.³ .............................................. A61B 5/02
[52] U.S. Cl. .................................. 128/642; 128/670; 128/715; 128/773; 128/786
[58] Field of Search ............... 128/642, 696, 715, 786, 128/802, 670, 349 B, 773, 671

[56] References Cited

U.S. PATENT DOCUMENTS

| 3,326,207 | 6/1967 | Egan | 128/642 |
|---|---|---|---|
| 3,339,542 | 9/1967 | Howell | 128/736 |
| 3,951,136 | 4/1976 | Wall | 128/715 X |
| 4,090,518 | 5/1978 | Elam | 128/696 X |
| 4,176,660 | 12/1979 | Mylrea | 128/715 X |

OTHER PUBLICATIONS

Med. & Biol. Engng., vol. 7, (1969), pp. 341–343.
Anethesia & Analgesia, vol. 44, No. 1, Jan.-Feb., (1964).

Primary Examiner—Kyle L. Howell
Attorney, Agent, or Firm—Powell L. Sprunger

[57] ABSTRACT

An esophageal probe comprising, a shaft assembly having an elongated shaft with an inflation lumen extending along the shaft, and an inflatable balloon on the shaft communicating with the inflation lumen. The probe has a pair of conductive electrodes on an outer surface of the balloon.

7 Claims, 2 Drawing Figures

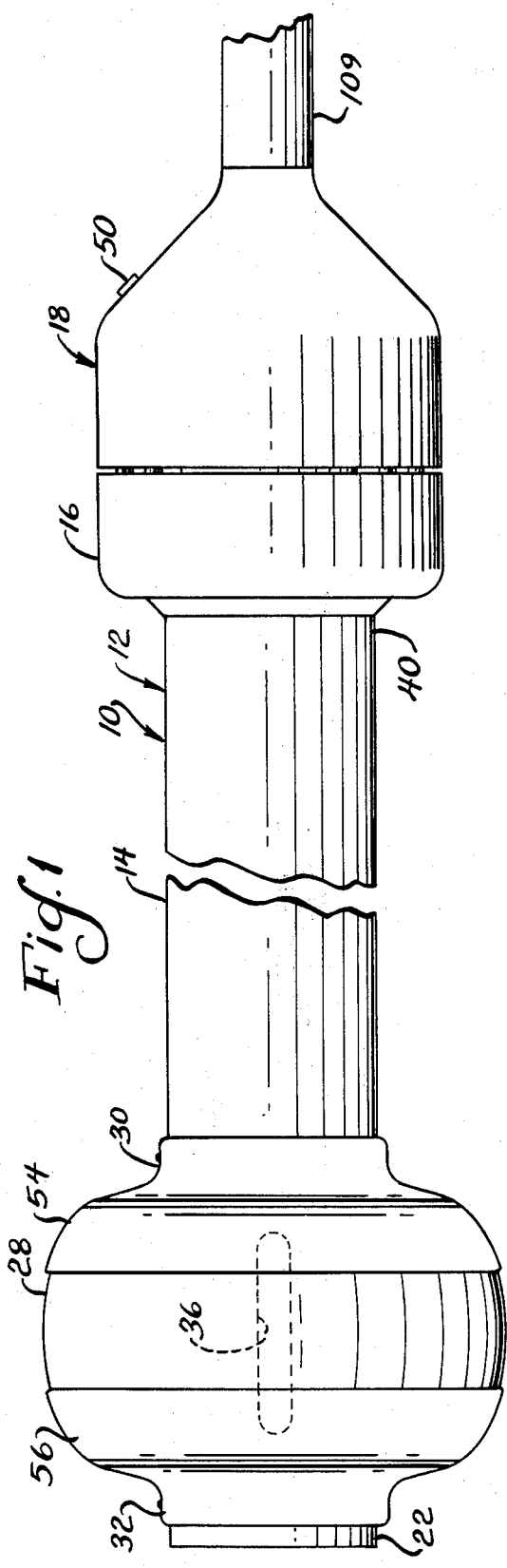
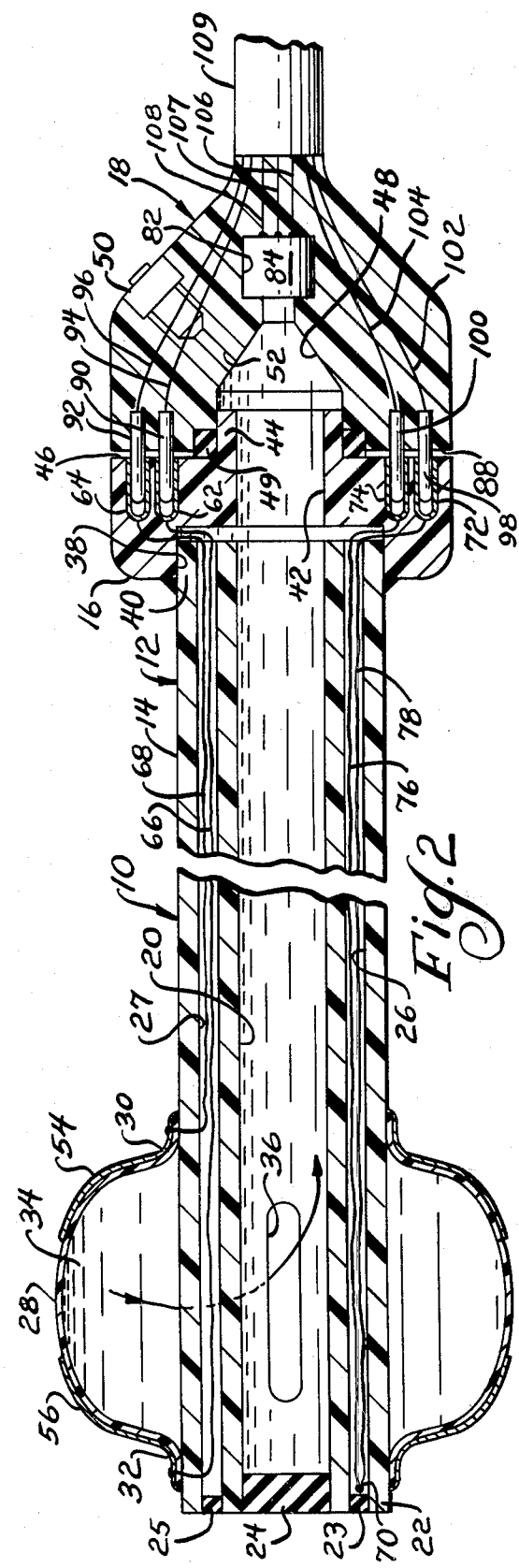

ESOPHAGEAL PROBE WITH BALLOON ELECTRODE

BACKGROUND OF THE INVENTION

The present invention relates to monitoring devices, and more particularly to esophageal probes.

An assortment of esophageal probes have been proposed for insertion into the esophagus of a patient to monitor body functions of the patient. A number of the probes have had ECG electrodes on an outer surface of the probe shaft. However, it is desirable to obtain improved contact with the electrodes in the patient's body.

SUMMARY OF THE INVENTION

A principal feature of the present invention is the provision of an improved esophageal probe for use in a patient.

The esophageal probe comprises a shaft assembly comprising an elongated shaft having an inflation lumen extending through the shaft and communicating with an opening adjacent a distal end of the shaft, and a balloon adjacent the distal end of the shaft. The balloon comprises a cylindrical sleeve of elastic material having opposed ends bonded to the shaft in circumferential zones, with the sleeve defining a cavity communicating with the opening. The probe has a pair of annular spaced conductive electrodes adjacent opposed ends of the sleeve on an outer surface of the sleeve.

A feature of the present invention is that the balloon may be inflated through the inflation lumen of the shaft.

Yet another feature of the invention is that the electrodes on the outer surface of the balloon make improved contact with the patient's body when the balloon is inflated.

Further features will become more fully apparent in the following description of the embodiments of this invention and from the appended claims.

DESCRIPTION OF THE DRAWINGS

In the drawings:

FIG. 1 is a fragmentary elevational view of an esophageal probe of the present invention; and FIG. 2 is a fragmentary elevational view, taken partly in section, of the esophageal probe of FIG. 1.

DESCRIPTION OF THE PREFERRED EMBODIMENTS

Referring now to FIGS. 1 and 2, there is shown an esophageal probe generally designated 10 having a shaft assembly 12 comprising an elongated shaft 14 and proximal first connector 16, with the probe 10 also having a second proximal connector or plug 18. As shown, the shaft 14 has a first inflation lumen 20 extending through the shaft and being closed at a distal end 22 of the shaft by a suitable plug 24, and second and third lumens 26 and 27, respectively, extending through the shaft and being closed by plugs 23 and 25 at the distal end 22 of the shaft 14. The shaft assembly 12 also has an inflatable balloon 28 comprising a cylindrical sleeve of elastic material having first and second opposed end portions 30 and 32 being secured to an outer surface of the shaft 14 in circumferential zones, such that the balloon 28 defines a cavity 34 communicating with the inflation lumen 20 through an elongated opening 36 in an outer wall of the shaft 14.

The first connector 16 has a recess 38 to receive a proximal end 40 of the shaft 14, such that the first connector 16 may be secured to the shaft 14 through suitable means, such as by adhesive. The first connector 16 has a bore 42 extending through the first connector 16, with a tubular extension 44 extending from a proximal face 46 of the first connector 16 defining a proximal portion of the inflation lumen 20. The second connector 18 has a distal recess 48 to receive the tubular extension 44 and define a proximal end of the inflation lumen 20. The second connector 18 also has an elastic O-ring 49 at a distal end to make sealing engagement with an outer surface of the tubular extension 44. The second connector 18 also has valve means 50 of known type communicating with the inflation lumen 20 through a side channel 52. When a syringe is attached to the valve means 50, the valve means 50 permits passage of liquid from the syringe through the valve means 50 in order to fill the inflation lumen 20 and cavity 34 with the liquid while inflating the balloon 20. Also, the liquid in the inflation lumen 20 may be removed through the valve means 50 by use of the syringe.

The shaft assembly 12 has spaced first and second annular conductive ECG electrodes 54 and 56 of flexible material extending circumferentially around the balloon 28 on an outer surface of the balloon, with the first proximal electrode 54 extending from a central portion to a proximal end of the balloon 28, and with the second distal electrode extending from a central portion to a distal end of the balloon 28. The electrodes 54 and 56 may be made of a suitable conductive material, such as metallic paint or metallic foil placed on the outer surface of the balloon 28. The first connector 16 has recesses in the proximal face 46 of the first connector 16 to receive sockets 62 and 64 of conductive material, such as metal. The shaft assembly 12 has a conductive lead 66 connected to the socket 62 and extending through the first connector 16 and the lumen 27 to the distal end of the balloon 28 where it is connected to the distal end of the second electrode 56 in order to establish electrical connection between the socket 62 and the second electrode 56. The shaft assembly 12 also has a conductive lead 68 connected to the socket 64 and extending through the first connector 16 and the lumen 27 to the proximal end of the balloon 28 where it is connected to the proximal end of the first electrode 54 in order to establish electrical connection between the first electrode 54 and the socket 64.

As shown, the shaft assembly 12 has a temperature sensor 70 in the second shaft lumen 26 adjacent the distal end 22 of the shaft 14. The first connector 16 has a pair of recesses in the proximal face 46 of the first connector 16 to receive a pair of conductive sockets 72 and 74, such as metal. The shaft assembly 12 also has a pair of conductive leads 76 and 78 connected to the sockets 72 and 74, respectively, and extending through the first connector 16 and through the lumen 26 to the temperature sensor 70. In this manner, electrical connection is made between the sensor 70 and the sockets 72 and 74. The shaft 14 may be made of suitable plastic material, such as polyvinylchloride, and the balloon 28 may be made of suitable elastic material, such as rubber. The first and second connectors 16 and 18 may also be made of suitable plastic material, such as polyvinylchloride.

With reference to FIGS. 1 and 2, the second connector 18 has a central cavity 82 to receive a vibration detection device 84, such as a microphone or hydrophone, hereinafter microphone, with the recess 48 extending from the microphone 84 to a distal face 88 of the second connector 18. The second connector 18 has a pair of conductive pins 90 and 92 extending from the distal face 88 of the second connector 18 and receivable in the sockets 62 and 64, respectively, with the second connector 18 having a pair of conductive leads 94 and 96 extending from the pins 90 and 92, respectively, through the second connector 18 to a proximal end thereof. The second connector 18 also has a pair of conductive pins 98 and 100 extending from the distal face 88 of the second connector 18 and receivable in the sockets 72 and 74, respectively, with the second connector 18 having a pair of conductive leads 102 and 104 extending from the pins 98 and 100, respectively, through the second connector 18 to a proximal end thereof. The second connector 18 also has conductive leads 106, 107, and 108 extending from the microphone 84 through the second connector 18 to a proximal end of the second connector 18. The proximal ends of the leads 94, 96, 102, 104, 106, 107, and 108 may be formed into a cable 109 connected to the proximal end of the second connector 18.

When the second connector 18 is attached to the first connector 16, the pins 90, 92, 98, and 100 are frictionally received in the sockets 62, 64, 72, and 74, respectively, in order to establish electrical contact between the pins and sockets and releasably attach the second connector 18 to the first connector 16. In the attached configuration of the connectors, the pins and sockets establish electrical connection between the lead 94 and the second electrode 56 through the lead 66, between the lead 96 and the first electrode 54 through the lead 68, and between the leads 102 and 104 and the temperature sensor 70 through the leads 76 and 78. In this manner, electrical connection is made between the second connector 18 and the electrical components in the shaft assembly 12. Also, as shown in FIG. 2, when the second connector 18 is attached to the first connector 16, the proximal end of the inflation lumen 20 is located adjacent the microphone 84. Thus, sounds occurring adjacent the balloon 28 are transmitted by the liquid in the cavity 34 and inflation lumen 20 to the microphone 84. In this manner, sounds are detected by the microphone 84 when the probe is located in the patient's body.

In use, the shaft 14 of the probe 10 is inserted into the esophagus of a patient with the balloon in an uninflated condition. Next, a syringe is attached to the valve means 50, and liquid is pumped from the syringe through the valve means 50 into the inflation lumen 20 in order to fill the inflation lumen 20 and the cavity 34 while inflating the balloon 28. The leads 106, 107, and 108 associated with the microphone 84 may be attached to suitable electrical equipment for monitoring sounds, with the sounds being transmitted through the sound conducting medium of the liquid in the cavity 34 and inflation lumen 20 in order to monitor heart and lung sounds occurring adjacent the inflatable balloon 28. Also, the leads 94 and 96, which are electrically connected to the first and second electrodes 54 and 56, may be connected to suitable ECG electrical monitoring equipment. Similarly, the leads 102 and 104, which are electrically connected to the temperature sensor 70, may be connected to suitable electrical equipment to indicate the temperature in the patient's body. Due to inflation of the balloon 28, the ECG electrodes 54 and 56 on the inflated balloon make improved contact with the patient's body in the esophagus.

After use of the probe 10 in the patient's body, the shaft 14 may be removed from the esophagus, and the first connector 16 of the shaft assembly 12 may be removed from the second connector 18, after which the used shaft assembly 12 may be discarded. The second connector 18 may then be attached to another shaft assembly 12 of the same type in order to use the esophageal probe 10 on another patient. In this manner, the shaft assembly 12 is rendered disposable, while the relatively expensive microphone 84 in the second connector 18 may be utilized with a number of shaft assemblies 12 on different patients.

The foregoing detailed description is given for clearness of understanding only, and no unnecessary limitations should be understood therefrom, as modifications will be obvious to those skilled in the art.

I claim:

1. An esophageal probe, comprising:
   a shaft assembly comprising an elongated shaft having a distal end, a proximal end, an inflation lumen extending along the shaft, and an inflatable balloon on the shaft communicating with the inflation lumen; and
   at least one conductive electrode on an outer surface of said balloon, said shaft assembly including a first connector adjacent the proximal end of the shaft, and including a second connector releasably attached to the first connector, means for establishing electrical connection between the attached first and second connectors, and conductive means connecting said electrode to the electrical establishing means, said inflation lumen extending through the first connector and into said second connector, and said shaft assembly having valve means in the second connector communicating with the inflation lumen to inflate and deflate the balloon.

2. The probe of claim 1 wherein the balloon is located adjacent a distal end of the shaft.

3. The probe of claim 1 wherein the balloon comprises a cylindrical sleeve being bonded to the shaft in circumferential zones adjacent opposed ends of the sleeve.

4. The probe of claim 3 wherein the probe has a pair of spaced annular electrodes in circumferential zones adjacent proximal and distal ends of said sleeve.

5. The probe of claim 1 wherein the probe has a pair of spaced conductive electrodes on the outer surface of the balloon.

6. The probe of claim 1 wherein the electrical establishing means comprises a plurality of conductive sockets in one of said connectors and a plurality of conductive pins on the other of said connectors, said pins being received in the sockets when the first connector is attached to the second connector.

7. An esophageal probe, comprising:
   a shaft assembly comprising an elongated shaft having a distal end, a proximal end, an inflation lumen extending through the shaft and communicating with an opening adjacent the distal end of the shaft, and an inflatable balloon adjacent the distal end of the shaft, said balloon comprising a cylindrical sleeve of elastic material having opposed ends bonded to the shaft in circumferential zones, said sleeve defining a cavity communicating with said opening; and
   a pair of annular spaced conductive electrodes adjacent opposed ends of the sleeve on an outer surface of the sleeve, said electrodes extending completely circumferentially around the sleeve in circumferential zones, and a pair of conductive leads connected to said electrodes.

* * * * *